«12» United States Patent
Park et al.

(10) Patent No.: US 8,101,214 B2
(45) Date of Patent: Jan. 24, 2012

(54) COMPOSITION FOR SKIN EXTERNAL APPLICATION CONTAINING COMPLEX OF HERBAL EXTRACTS

(75) Inventors: Jun Seong Park, Gyeonggi-do (KR); Jin Young Lee, Gyeonggi-do (KR); Eun Joo Kim, Gyeonggi-do (KR); Hye Yoon Park, Gyeonggi-do (KR); Sung Il Park, Seoul (KR); Youn Joon Kim, Seoul (KR); Duck Hee Kim, Seoul (KR); Ih Seop Chang, Gyeonggi-do (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 12/745,064

(22) PCT Filed: Nov. 13, 2008

(86) PCT No.: PCT/KR2008/006698
§ 371 (c)(1),
(2), (4) Date: Sep. 27, 2010

(87) PCT Pub. No.: WO2009/069906
PCT Pub. Date: Jun. 4, 2009

(65) Prior Publication Data
US 2011/0014149 A1    Jan. 20, 2011

(30) Foreign Application Priority Data
Nov. 30, 2007 (KR) .................. 10-2007-0123526

(51) Int. Cl.
*A61K 36/00* (2006.01)
*A61K 8/97* (2006.01)
*A61K 36/736* (2006.01)

(52) U.S. Cl. .................... 424/725; 424/74; 424/735

(58) Field of Classification Search .................. None
See application file for complete search history.

(56) References Cited

U.S. PATENT DOCUMENTS

2006/0018867 A1* 1/2006 Kawasaki et al. ........ 424/70.122
2008/0131384 A1    6/2008 Maeda et al.

FOREIGN PATENT DOCUMENTS

| JP | 2003-061329 | * | 6/2002 |
| JP | 2003113028 A | * | 4/2003 |
| KR | 2000-49466 | | 8/2000 |
| KR | 2007-232060 | * | 1/2007 |
| KR | 2007-80669 | | 8/2007 |
| KR | 2008-C44282 | * | 8/2007 |

OTHER PUBLICATIONS

International Search Report for PCT/KR2008/006698, mailed Apr. 28, 2009.

* cited by examiner

*Primary Examiner* — Melenie McCormick
*Assistant Examiner* — Randall Winston
(74) *Attorney, Agent, or Firm* — Nixon & Vanderhye P.C.

(57) ABSTRACT

Disclosed is a combination for skin external use, which contains as an active ingredient an herbal extract complex consisting of Chinese herbal extracts of Granate bark, seed of *Prunus armeniaca, Coix lacuma-jobi, Saururus chinensis* and *Perilla frutescens* var. *acuta*. More particularly, disclosed is a composition for skin external use containing an herbal extract complex, which is prepared by mixing the Chinese herbs with each other at an optimal ratio to prepare an herbal mixture and extracting the herbal mixture to prepare an herbal extract complex, and thus shows the effects of promoting the differentiation of skin keratinocytes, restoring impaired skin barrier function and increasing skin moisturization compared to extracts obtained by extracting each of the herbs alone.

13 Claims, 1 Drawing Sheet

COMPOSITION FOR SKIN EXTERNAL APPLICATION CONTAINING COMPLEX OF HERBAL EXTRACTS

This application is the U.S. national phase of International Application No. PCT/KR2008/006698 filed 13 Nov. 2008, which designated the U.S. and claims priority to Korean Application No. 10-2007-0123526 filed 30 Nov. 2007, the entire contents of each of which are hereby incorporated by reference.

TECHNICAL FIELD

The present invention relates to a composition for skin external use, which contains as an active ingredient an herbal extract complex consisting of Chinese herbal extracts of Granate bark, seed of *Prunus armeniaca, Coix lacryma-jobi, Saururus chinensis* and *Perilla frutescens* var. *acuta*, and more particularly to a composition for skin external use containing an herbal extract complex, which is prepared by mixing said Chinese herbs with each other at an optimal ratio to prepare an herbal extract and extracting the herbal mixture to prepare an herbal extract complex, and thus shows the effects of promoting the differentiation of skin keratinocytes, restoring impaired skin barrier function and increasing skin moisturization compared to extracts obtained by extracting each of the herbs alone.

BACKGROUND ART

The skin plays a very important role as a barrier protecting the body from the external environment. This barrier function is a protective function of defending the body from various external stimuli (e.g., chemicals, pollutants, dry environments, UV rays, etc.) and protecting the excessive loss of water from the body through the skin. This protective function can be maintained only when the horny layer consisting of keratinocytes is normally formed.

The Stratum corneum (horny layer) which is the outermost layer of the epidermis is formed of keratinocytes and consists of differentiated keratinocytes and lipid layers surrounding them (Marcelo C. L. et al, *J. Invest. Dermatol.*, 80, pp. 37-44, 1983).

Keratinocytes are characteristic cells formed as basal cells that continuously proliferate in the lowest layer of the epidermis move up toward the skin's surface while they undergo stepwise changes in their morphology and function. After a given period of time, old keratinocytes are removed from the skin and replaced with new keratinocytes, and such a series of repeated changes is called "differentiation of epidermal cells" or "keratinization".

In the keratinization process, keratinocytes form the horny layer while producing natural moisturizing factor (NMFs) and intracellular lipids (ceramide, cholesterol, fatty acid, etc.), such that the horny layer has firmness and flexibility so as to function as a skin barrier.

This horny layer can readily lose its function due to habitual factors such as excessive face washing or bathing, environmental factors such as dry pollutants, and endogenous diseases such as atopic skin or senile skin. In fact, due to various factors which are further increasing these days, people suffering from dry skin and various symptoms caused thereby are gradually increasing.

Accordingly, various studies have been conducted in order to supply water from the outside or prevent the loss of water from the body so as to maintain the skin water content at a suitable level. In fact, various moisturizers having water holding ability have been developed. As skin moisturizers, lipid components such as ceramide, and substances such as essential fatty acids and lipid complexes which can increase water holding in the horny layer are generally used (Rawlings A. V. et al, *J. Invest. Dermatol.*, 5, pp. 731-741, 1994).

However, the risky factors for the skin gradually increase, the production and removal rates of the horny layer become slow due to the change of eating habits, the amount of moisturizing factors and lipids in the horny layer is decreased due to deterioration in the function of keratinocytes, and for these reasons, people having skins, the horny layer of which does not exhibit a normal skin barrier function, gradually increase. This breakdown of the skin barrier function will cause various skin diseases including dry skin, atopic dermatitis, contact dermatitis and psoriasis. Such diseases can be alleviated only by existing conventional moisturizers having water-holding function, but the fundamental treatment thereof with the conventional moisturizers is difficult.

As used herein, the term "Granate bark" refers to the cortex of the fruit, stem, branch and root of *Punica granatum* L. The plant *Punica granatum* L. has a yellow or yellowish red color when ripened. Also, the plant is a fleshy plant, and the outer bark often irregularly breaks to show seeds. In Chinese herbal medicine, the plant is used as a drug for stopping diarrhea, inhibiting intestinal bleeding, treating oral mucositis and tonsillitis, controlling insects, and preventing miscarriage and conception.

Seed of *Prunus armeniaca* refers to a dried seed obtained by removing a fruit flesh and a seed coat from the ripe fruit of an apricot tree belonging to the family Rosaceae. In Chinese herbal medicine, it is known to be effective in treating cough and asthma. Particularly, it has been reported to contain a large amount of unsaturated fatty acids, and thus have an excellent effect of relieving and softening the skin and also an excellent skin whitening effect.

*Coix lacryma-jobi* is the seed of Job's tears belonging to the family Gramineae. In Chinese herbal medicine, it is used to treat diarrhea, dropsy, headache and muscle cramp. The effective components thereof include coixol and sitosterol.

*Saururus chinensis* is a perennial dicotyledonous plant belonging to the family Saururaceae of the order Piperales, and the root and stem thereof have a white color and spread sideways in mud. The leaves thereof cross each other and have a pointed tip and a heart-shaped bottom. The surface of the leaves has a green color, and the back surface has a light white color, but 2-3 leaves present at the upper portion of the stem have a white surface. In Chinese herbal medicine, the whole plant is dried and used to treat body swelling and abnormal urination and also to treat beriberi, jaundice and hepatitis.

*Perilla frutescens* var. *acuta* refers to the leaf of a beefsteak plant which is an annual plant belonging to the family Labiatae. The stem of the plant has a square shape, stands up straight and has a height of 20-80 cm. The leaf of the plant has a broad oval shape similar to that of *Perilla japonica*, but has a purple color and strong fragrance and includes a sawtooth edge. In Chinese herbal medicine, the whole plant including roots is known to be effective in treating anemia, inhibiting perspiration, alleviating fever, treating bronchitis, cough and asthma, loosening phlegm, treating gastroenteritis, promoting digestion, treating vertigo, alleviating body pain, alleviating nasal obstruction, and reducing nasal discharge, and is used as an agent for treating poisoning by fishes.

DISCLOSURE

Technical Problem

Accordingly, the present inventors have conducted studies to find materials showing an excellent skin moisturizing effect from Chinese herbal materials and, as a result, have found that an herbal extract complex consisting of Chinese herbal extracts of Granate bark, seed of *Prunus armeniaca, Coix lacryma-jobi, Saururus chinensis* and *Perilla frutescens* var. *acuta* have the effects of moisturizing the skin, enhancing skin barrier function and inducing the differentiation of skin keratinocyte cells, thereby completing the present invention.

It is therefore an object of the present invention to maximize the extraction of effective components from said five kinds of Chinese herbal materials by adjusting the mixing ratio of the Chinese herbal materials to an optimal ratio, and to examine the effects of the extracted components on the promotion of differentiation of keratinocytes, the restoration of impaired skin barrier function and the increase in skin moisturization, and to provide a composition for moisturizing the skin, enhancing skin barrier function and inducing the differentiation of skin keratinocytes on the basis of the examination results.

Technical Solution

To achieve the above object, the present invention provides a composition for skin external use, which contains as an active ingredient an herbal extract complex consisting of Chinese herbal extracts of Granate bark, seed of *Prunus armeniaca, Coix lacryma-jobi, Saururus chinensis* and *Perilla frutescens* var. *acuta*.

The herbal extract complex according to the present invention is obtained by mixing Granate bark, seed of *Prunus armeniaca, Coix lacryma-jobi, Saururus chinensis* and *Perilla frutescens* var. *acuta* with each other at a weight ratio of 1:2:2:6-8:6-8 to prepare an herbal extract, and extracting the herbal mixture.

The composition for skin external use is used to moisturize the skin, enhance the skin barrier function and induce the differentiation of skin keratinocytes.

Advantageous Effects

The herbal extract complex according to the present invention, which consists of an herbal extract complex consisting of Chinese herbal extracts of Granate bark, seed of *Prunus armeniaca, Coix lacryma-jobi, Saururus chinensis* and *Perilla frutescens* var. *acuta*, shows the effects of promoting the differentiation of keratinocytes, restoring impaired skin barrier function and increasing skin moisturization. Thus, the skin external composition containing the herbal extract complex will be useful as a cosmetic composition or pharmaceutical composition not only for preventing or ameliorating dry skin, atopic dermatitis, contact dermatitis or psoriasis, which occurs due to incomplete epidermal differentiation, but also for moisturizing the skin, enhancing skin barrier function and inducing the differentiation of skin keratinocytes.

BEST MODE

Figure 1:
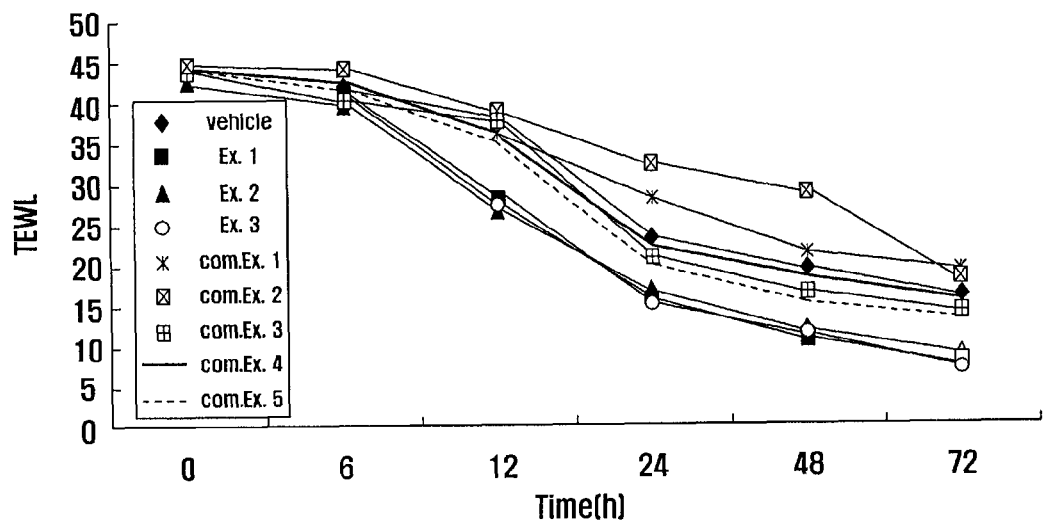
FIG. 1 is a graph showing the effect of the inventive herbal extract complex on the restoration of impaired skin barrier function.

The present invention provides a composition for skin external use containing as an active ingredient an herbal extract complex consisting of Chinese herbal extracts of Granate bark, seed of *Prunus armeniaca, Coix lacryma-jobi, Saururus chinensis* and *Perilla frutescens* var. *acuta*.

Hereinafter, the present invention will be described in detail.

The present invention provides a composition for skin external use which contains an herbal extract complex prepared by mixing Granate bark, seed of *Prunus armeniaca, Coix lacryma-jobi, Saururus chinensis* and *Perilla frutescens* var. *acuta* with each other at a dry weight ratio of 1:2:2:6-8:6-8 and extracting the mixture. In the present invention, extracts prepared from the above-described herbal materials at various mixing ratios were tested for their effects and, as a result, they showed the most excellent effects in the above-specified mixing ratio range.

An extraction solvent which is used in the resent invention may be any one or a mixed solvent of two or three selected from the group consisting of purified water, methanol, ethanol, glycerin, ethyl acetate, butylene glycol, prolylene glycol, dichloromethane and hexane.

The extract in the present invention is preferably either a liquid phase extract obtained by cold soaking at room temperature, heating and filtration or an extract obtained by evaporating the solvent from the liquid phase extracts or spray-drying or freeze-drying the liquid phase extracts.

The skin external composition according to the present invention contains the herbal extract complex in an amount of 0.0001-20 wt % based on the total weight of the composition. If the content of the herbal extract complex is less than 0.0001 wt %, the herbal extract complex cannot show the effects of moisturizing the skin, enhancing the skin's barrier function and inducing the differentiation of skin keratinocytes, and if the content exceeds 20 wt %, the increase in the content will not lead to a significant increase in the effects of the composition and can cause problems in the touch feel and formulation stability of the product.

The composition for skin external use containing the herbal extract complex can be used to moisturize the skin, enhance the skin's barrier function and induce the differentiation of skin keratinocytes. Thus, the composition can be advantageously used as a skin external composition for preventing or ameliorating dry skin, atopic dermatitis, contact dermatitis and psoriasis which occur due to incomplete epidermal differentiation.

The composition for skin external use according to the present invention may be formulated into cosmetic compositions such as skin lotion, astringent lotion, milk lotion, nourishing cream, massage cream, essence, eye cream, eye essence, cleansing cream, cleansing foam, cleansing water, pack, powder, body lotion, body cream, body oil, body essence, makeup base, foundation, hair-dyeing agent, shampoo, rinse or body cleaner, or into pharmaceutical compositions such as ointment, gel, cream, patch or spray, and there is no particular limitation on the formulation of the composition. The composition of the present invention may contain various bases and additives required for the formulation thereof, and the kinds and amounts of these components can be easily selected by one skilled in the art.

The formulation of the skin external composition according to the present invention will now be described in further detail.

In addition to the herbal extract complex, the cosmetic composition may contain other ingredients which may provide synergic effect to the main effect the present invention, as long as they do not impair the main effect of the present invention.

The herbal extract complex according to the present invention is preferably prepared in the form of cosmetic formulations which are applied directly on the skin, but it may also be in the form of conventional skin external formulations.

The additive ingredients may be properly selected and combined by a person in the art according to the formulation and purpose of the cosmetic composition.

The cosmetic composition may comprise a skin absorption promoter in order to increase the effects of moisturizing the skin, enhancing the skin's barrier function and inducing the differentiation of skin keratinocytes.

In addition, the cosmetic composition of the present invention may additionally contain one or more selected from the group consisting of water-soluble vitamins, oil-soluble vitamins, polymeric peptides, sphingolipids and seaweed extracts, which are conventionally added to a cosmetic composition.

Moreover, the cosmetic composition according to the present invention may further comprise an additive, which is commonly added to a cosmetic composition, as needed, in addition to the essential ingredients. Examples of the includes oily components, moisturizers, emollients, surfactants, organic and inorganic pigments, organic powders, UV ray absorbents, preservatives, antibacterial agents, antioxidants, plant extracts, pH regulators, alcohols, colorants, perfumes, blood circulation promoters, cooling agents, anti-perspiration agents, purified water and the like.

The pharmaceutical composition comprising the herbal extract complex of the present invention may further comprise a suitable carrier, excipient and diluent, which are conventionally used for the preparation of pharmaceutical compositions.

The pharmaceutical composition containing the herbal extract complex according to the present invention may be formulated according to any conventional method without any particular limitation. Examples of the formulation include skin external formulations such as ointment, gel, cream, patch or spray.

Although the dose of the formulation according to the present invention varies depending on the patient's age, sex, weight and condition, and the mode of administration, the formulation is preferably applied in an amount 1.0-2.0 ml/day 1-5 times for one month or more.

Meanwhile, the herbal extract complex of the present invention has little or no toxicity and side effects, and thus can be safely used for preventive purposes for a long period of time.

MODE FOR INVENTION

Hereinafter, the present invention will be described in further detail with reference to examples and test examples, but the scope of the present invention is not limited only to these examples.

Example 1

Preparation 1 of Herbal Extract Complex

Granate bark, seed of *Prunus armeniaca, Coix lacryma-jobi, Saururus chinensis* and *Perilla frutescens* var. *acuta*, which had been dried, were mixed with each other at a weight ratio of 1:2:2:7:6 to prepare 2 kg of an herbal mixture. The herbal mixture was added to 5 l of 80% ethanol aqueous solution, extracted three times under reflux and then soaked at 15° C. for 1 day. Then, the solution was subjected to filtration through filter cloth and centrifugation to separate it into residue and a filtrate. The separated filtrate was concentrated under reduced pressure, and the concentrate was suspended in water and extracted five times with 1 liter of ether to remove pigments. The aqueous layer was extracted three times with 500 ml of 1-butanol. The resulting total 1-butanol layer was concentrated under reduced pressure to obtain a 1-butanol extract. The extract was dissolved in a small amount of methanol, and then a large amount of ethyl acetate was added thereto. The produced precipitate was dried, thus obtaining 200 g of an herbal extract complex.

Example 2

Preparation 2 of Herbal Extract Complex

Dried Granate bark, seed of *Prunus armeniaca, Coix lacryma-jobi, Saururus chinensis* and *Perilla frutescens* var. *acuta*, which had been dried, were mixed with each other at a weight ratio of 1:2:2:7:7 to prepare 2 kg of an herbal mixture. The herbal extract was extracted in the same manner as in Example, thus obtaining 150 g of an herbal extract complex.

Example 3

Preparation 3 of Herbal Extract Complex

Dried Granate bark, seed of *Prunus armeniaca, Coix lacryma-jobi, Saururus chinensis* and *Perilla frutescens* var. *acuta*, which had been dried, were mixed with each other at a weight ratio of 1:2:2:7:8 to prepare 2 kg of an herbal mixture. The herbal extract was extracted in the same manner as in Example, thus obtaining 170 g of an herbal extract complex.

Comparative Example 1

Preparation of Granate Bark Extract 2 kg of dried Granate bark was prepared, added to 2 l of 80% ethanol aqueous, extracted three times under reflux, and then soaked at 15° C. for 1 day. Then, the solution was subjected to filtration through filter cloth and centrifugation to separate it into residue and a filtrate. The separated filtrate was concentrated under reduced pressure, and the concentrate was suspended in water and extracted five times with 1 liter of ether to remove pigments. The aqueous layer was extracted three times with 500 ml of 1-butanol. The resulting total 1-butanol layer was concentrated under reduced pressure to obtain a 1-butanol extract. The extract was dissolved in a small amount of methanol, and then a large amount of ethyl acetate was added thereto. The produced precipitate was dried, thus obtaining 180 of a Granate bark extract.

Comparative Example 2

Preparation of Seed of *Prunus Armeniaca* Extract 2 kg of dried seed of *Prunus armeniaca* was extracted in the same manner as in Comparative Example 1, thus preparing 195 g of a seed of *Prunus armeniaca* extract.

Comparative Example 3

Preparation of *Coix Lacryma-Jobi* Extract 2 kg of dried *Coix lacryma-jobi* was extracted in the same manner as in Comparative Example 1, thus preparing 210 g of a *Coix lacryma-jobi* extract.

Comparative Example 4

Preparation of *Saururus Chinensis* Extract 2 kg of dried *Saururus chinensis* was extracted in the same manner as in Comparative Example 1, thus preparing 150 g of a *Saururus chinensis* extract.

Comparative Example 5

Preparation of *Perilla Frutescens* Var. *Acuta* Extract 2 kg of dried *Perilla frutescens* var. *acuta* was extracted in the same manner as in Comparative Example 1, thus preparing 130 g of a *Perilla frutescens* var. *acuta* extract.

Test Example 1

Effect of Promoting Differentiation of Keratinocytes

In order to examine the keratinocyte differentiation-promoting effects of the extracts obtained in Examples 1 to 3 and Comparative Examples 1 to 5, the amount of Cornified Envelops (CE) produced in the differentiation of keratinocytes was measured using absorbance in the following manner.

First, human keratinocytes, which have been isolated from the epidermis of new-born infants and primarily cultured, were placed in a culture flask and attached to the bottom of the flask. After this, the cells were treated with 1 ppm of each of the test substances shown in Table 1 below, and then cultured for 5 days to a confluence of about 70-800. Herein, the group treated with low calcium (0.03 mM), and the group treated with high calcium (1.2 mM), were used as a negative control group and a positive control group. Then, the cultured cells were harvested and washed with PBS (phosphate buffered saline), and then 1 ml of 1 mM Tris-HCl (pH 7.4) containing 20 mM DTT (dithiothreitol) and 2% SDS (sodium dodecyl sulfate) was added thereto. Then, the cell solution was sonicated boiled and centrifuged, and the precipitate was suspended in 1 ml of PBS and measured for absorbance at 340 nm. Meanwhile, a portion of the solution after the sonication was taken and measured for protein content which was used as a standard for evaluating the degree of cell differentiation. The measurement results are shown in Table 1 below.

TABLE 1

| Test substances | Differentiation (%) of keratinocytes |
| --- | --- |
| Low-calcium (0.03 mM) solution (negative control group) | 100 |
| High-calcium (1.2 mM) solution (positive control group) | 210 |
| Example 1 | 178 |
| Example 2 | 176 |
| Example 3 | 173 |
| Comparative Example 1 | 111 |
| Comparative Example 2 | 103 |
| Comparative Example 3 | 95 |
| Comparative Example 4 | 115 |
| Comparative Example 5 | 127 |

As shown in Table 1, it could be confirmed that, when the keratinocytes were treated with Examples 1 to 3 which were herbal extract complexes each consisting of five kinds of herbal materials, the degree of differentiation of the keratinocytes was significantly high compared to when the keratinocytes were treated with Comparative Examples 1 to 5 which were extracts consisting of each of the herbal materials.

Test Example 2

Measurement of the Effects of Restoring Skin Barrier Function and Skin Moisturization in Hairless Mouse Skin In order to measure the effects of the herbal extract complex on the restoration of the skin barrier function impaired due to skin damage and on the increase in skin moisturization, the following test was carried out.

First, the back of 8-10-week-old hairless mice (Charles River, Japan) was periodically applied with acetone twice a day for 5 days to induce the loss of skin barrier function in the skin of the back of the test animals. Then, the transepidermal water loss (TEWL) of the skin of the back was measured with an evaporimeter. Based on the measurement results, on only test animals having a skin showing a transepidermal water loss (TEWL) of more than 40 $g/m^2/hr$ were selected, and each of a vehicle consisting of a 7:3 mixture of propylene glycol and ethanol (vehicle-treated group) and a sample containing 1 wt % of each of the extracts prepared in Examples 1 to 3 and Comparative Examples 1 to 5 was continuously applied to the selected animals at a dose of 200 µl per 5 $cm^2$ of skin area twice a day for 3 days, while the TEWL of the skin was measured at given time intervals. The measurement results are shown in FIG. 1.

As can be seen from the results of FIG. 1, the impaired barriers of the groups treated with the extracts of Examples 1 to 3 were restored faster than those in the groups treated with the vehicle and the extracts of Comparative Examples 1 to 5.

Figure 2:
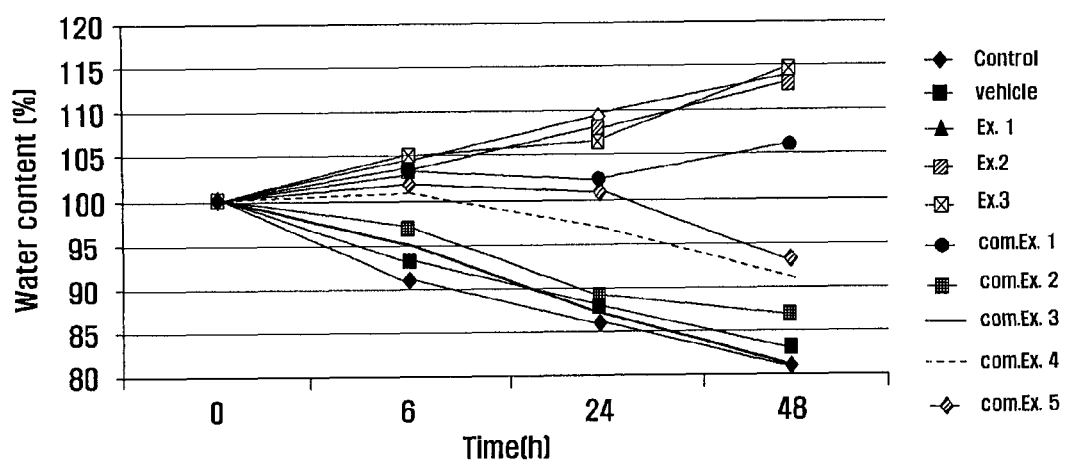
FIG. 2 is a graph showing the effect of the inventive herbal extract complex on skin moisturization.

Also, the water content of the skin was measured using a Corneometer (Courage Khazaka, Germany), and the measurement results are shown in FIG. 2. At this time, the water content of the skin in the control group was also measured.

As can be seen from the results of FIG. 2, the skin's water content was higher in the groups treated with the extracts of Examples 1 to 3 than in the groups treated with the extracts of Comparative Examples 1 to 5. Accordingly, it could be confirmed that treatment with the herbal extract complexes restored the impaired skin barriers and also increased the skin's water content.

From the results described above, it can be confirmed that the herbal extract complex of the present invention has very excellent effects of promoting the differentiation of keratinocytes, restoring impaired skin barriers and increasing skin moisturization.

Hereinafter, formulation examples of the composition according to the present invention will be described, but these formulation examples are for illustrative purposes only without limiting the scope of the present invention.

Formulation Example 1

Preparation of Soap

According to the composition shown in Table 2 below, soap of Formulation Example 1 was prepared by a conventional method (unit: wt %).

TABLE 2

| Components | Contents |
| --- | --- |
| Herbal extract complex of Example 1 | 1.00 |
| Oil and fat | q.s. |
| Sodium hydroxide | q.s. |
| Sodium chloride | q.s. |
| Perfume | Small amount |
| Purified water | Balance |

Formulation Example 2

Preparation of Lotion

According to the composition shown in Table 3, lotion of Formulation Example 2 was prepared by a conventional method (unit: wt %).

TABLE 3

| Components | Contents |
| --- | --- |
| Herbal extract complex of Example 1 | 3.00 |
| L-ascorbic acid-2-magnesium phosphate | 1.00 |
| Water-soluble collagen (1% aqueous solution) | 1.00 |
| Sodium citrate | 0.10 |
| Citric acid | 0.05 |
| Licorice extract | 0.20 |
| 1,3-butylene glycol | 3.00 |
| Purified water | Balance |

Formulation Example 3

Preparation of Cream

According to the composition shown in Table 4 below, cream of Formulation Example 3 was prepared by a convention method (unit: wt %).

TABLE 4

| Components | Contents |
| --- | --- |
| Herbal extract complex of Example 1 | 1.00 |
| Polyethyleneglycol monostearate | 2.00 |
| Self-emulsifying glycerin monostearate | 5.00 |
| Cetyl alcohol | 4.00 |
| Squalene | 6.00 |
| 2-ethylhexane glycerol | 6.00 |
| Sphingoglycolipid | 1.00 |
| 1,3-butylene glycol | 7.00 |
| Purified water | Balance |

Formulation Example 4

Preparation of Pack

According to the composition shown in Table 5 below, pack of Formulation Example 4 was prepared by a conventional method (unit: wt %).

TABLE 5

| Components | Contents |
| --- | --- |
| Herbal extract complex of Example 1 | 5.00 |
| Polyvinyl alcohol | 13.00 |
| L-ascorbic acid-2-magnesium phosphate | 1.00 |
| Lauroylhydroxyproline | 1.00 |
| Water-soluble collagen (1% aqueous solution) | 2.00 |
| 1,3-butylene glycol | 3.00 |
| Ethanol | 5.00 |
| Purified water | Balance |

Formulation Example 5

Preparation of Essence

According to the composition shown in Table 6 below, essence of Formulation Example 5 was prepared by a conventional method (unit: wt %).

TABLE 6

| Components | Contents |
| --- | --- |
| Herbal extract complex of Example 1 | 2.00 |
| Hydroxyethylene cellulose (2% aqueous solution) | 12.00 |
| Xanthan gum (2% aqueous solution) | 2.00 |
| 1,3-butylene glycol | 6.00 |
| Concentrated glycerin | 4.00 |
| Sodium hyaluronate (1% aqueous solution) | 5.00 |
| Purified water | Balance |

The invention claimed is:

1. A topical composition for moisturizing skin, enhancing skin barrier function and/or inducing the differentiation of skin keratinocytes, which contains as an active ingredient an effective amount of an herbal extract complex consisting of Granate bark, seed of *Prunus armeniaca, Coix lacryma-jobi, Saururus chinensis* and *Perilla frutescens* var. *acuta*.

2. The composition of claim 1, wherein the herbal extract complex is prepared by mixing Granate bark, seed of *Prunus armeniaca, Coix lacryma-jobi, Saururus chinensis* and *Perilla frutescens* var. *acuta* with each other at a weight ratio of 1:2:2:6-8:6-8 to prepare an herbal mixture and extracting the herbal mixture.

3. The composition of claim 1, wherein the herbal extract complex is contained in an amount of 0.0001-20 wt % based on the total weight of the composition.

4. The composition of claim 1, wherein the herbal extract complex is prepared by extraction using any one or a mixed solvent of two or three selected from the group consisting of purified water, methanol, ethanol, glycerin, ethyl acetate, butylene glycol, prolylene glycol, dichloromethane and hexane.

5. The composition of claim 1, wherein the herbal extract complex is either a liquid phase extract obtained by cold soaking at room temperature, heating or filtration or an extract obtained by evaporating a solvent from the liquid phase extract or spray-drying or freeze-drying the liquid phase extract.

6. The composition of claim 1, wherein the composition is formulated into a cosmetic composition selected from the group consisting of a skin lotion, astringent lotion, milk lotion, nourishing cream, massage cream, essence, eye cream, eye essence, cleansing cream, cleansing foam, cleansing water, pack, powder, body lotion, body cream, body oil, body essence, makeup base, foundation, hair-dyeing agent, shampoo, rinse and body cleaner.

7. The composition of claim 1, wherein the composition is formulated into a pharmaceutical composition selected from the group consisting of an ointment, gel, cream, patch and spray.

8. A method of moisturizing skin comprising topically topically applying to the skin an effective amount of a composition, which contains as an active ingredient an herbal extract complex consisting of Granate bark, seed of *Prunus armeniaca, Coix lacryma-jobi, Saururus chinensis* and *Perilla frutescens* var. *acuta*.

9. The method of claim 8, wherein the composition is continuously applied in an amount of 1.0-3.0 ml/day 1-5 times a day for 1 month or more.

10. A method for enhancing skin barrier function, comprising topically applying to the skin an effective amount of a composition which contains as an active ingredient an herbal extract complex consisting of Granate bark, seed of *Prunus armeniaca, Coix lacryma-jobi, Saururus chinensis* and *Perilla frutescens* var. *acuta*.

11. A method for inducing the differentiation of skin keratinocytes, comprising topically applying to the skin an effective amount of a composition which contains as an active ingredient an herbal extract complex consisting of Granate bark, seed of *Prunus armeniaca, Coix lacryma-jobi, Saururus chinensis* and *Perilla frutescens* var. *acuta*.

12. The method of claim 10, wherein the composition is continuously applied in an amount of 1.0-3.0 ml/day 1-5 times a day for one month or more.

13. The method of claim 11, wherein the composition is continuously applied in an amount of 1.0-3.0 ml/day 1-5 times a day for one month or more.

* * * * *